United States Patent [19]
Dalton

[11] Patent Number: 4,464,178
[45] Date of Patent: Aug. 7, 1984

[54] METHOD AND APPARATUS FOR ADMINISTRATION OF FLUIDS

[76] Inventor: Michael J. Dalton, 9432 Monticello Ave., Evanston, Ill. 60203

[21] Appl. No.: 325,045

[22] Filed: Nov. 25, 1981

[51] Int. Cl.³ .................... A61M 25/02; A61M 5/00
[52] U.S. Cl. .................... 604/174; 604/180; 128/DIG. 26
[58] Field of Search .............. 604/890, 891, 896, 897, 604/8, 9, 49, 93, 115, 116, 117, 134, 174, 133, 175, 178, 180, 179, 181, 183–185, 334, 247; 128/DIG. 26, 133

[56] References Cited

U.S. PATENT DOCUMENTS

| | | | |
|---|---|---|---|
| 2,814,294 | 11/1957 | Figge | 128/215 |
| 3,310,051 | 3/1967 | Schulte | 128/216 |
| 3,487,837 | 1/1970 | Petersen | 604/180 |
| 3,640,269 | 2/1972 | Delgado | 128/2 R |
| 3,765,414 | 10/1973 | Arlen | 128/260 |
| 3,783,868 | 1/1974 | Bokros | 604/891 |
| 3,796,217 | 3/1974 | Arlen | 604/891 |
| 3,896,806 | 7/1975 | Wichterle | 604/891 |
| 3,951,147 | 4/1976 | Tucker et al. | 604/891 |
| 3,957,048 | 5/1976 | Jacobs | 128/214 R |
| 3,971,376 | 7/1976 | Wichterle | 128/260 |
| 4,080,970 | 3/1978 | Miller | 604/174 |
| 4,133,312 | 1/1979 | Burd | 604/8 |
| 4,141,361 | 2/1979 | Snyder | 604/133 |
| 4,190,048 | 2/1980 | Sampson | 128/215 |
| 4,232,677 | 11/1980 | Leibinsohn | 604/247 |
| 4,261,363 | 4/1981 | Russo | 128/350 R |
| 4,300,557 | 11/1981 | Refojo et al. | 604/891 |

FOREIGN PATENT DOCUMENTS 2901302  7/1980  Fed. Rep. of Germany ...... 604/180

Primary Examiner—C. Fred Rosenbaum
Assistant Examiner—Michelle N. Lester
Attorney, Agent, or Firm—Richard L. Hansen

[57] ABSTRACT

A delivery system for therapeutic fluids including an implantable fluid receptacle and means to anchor a transcutaneous fluid delivery conduit on the surface of the body, together with a method of using the system for the long-term administration of fluids to selected sites in the body.

11 Claims, 11 Drawing Figures

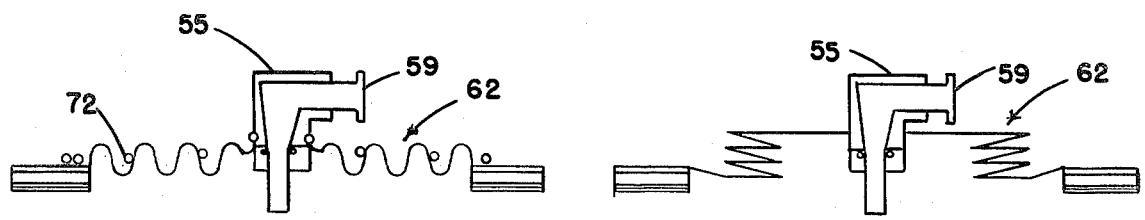
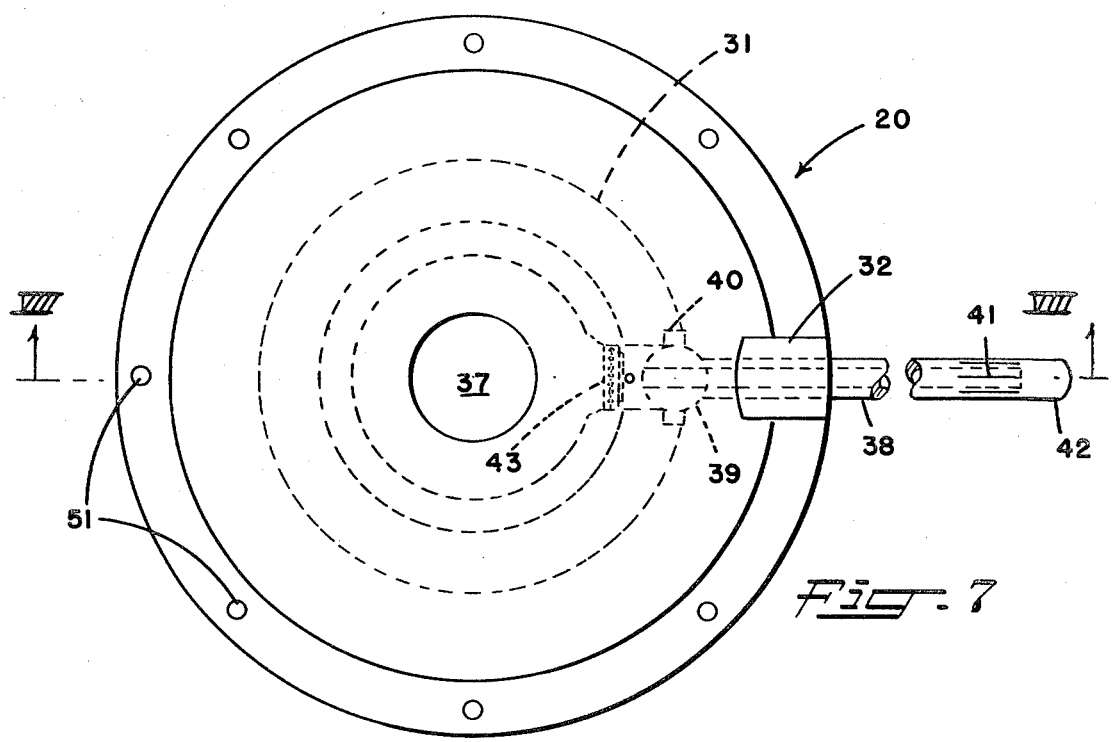
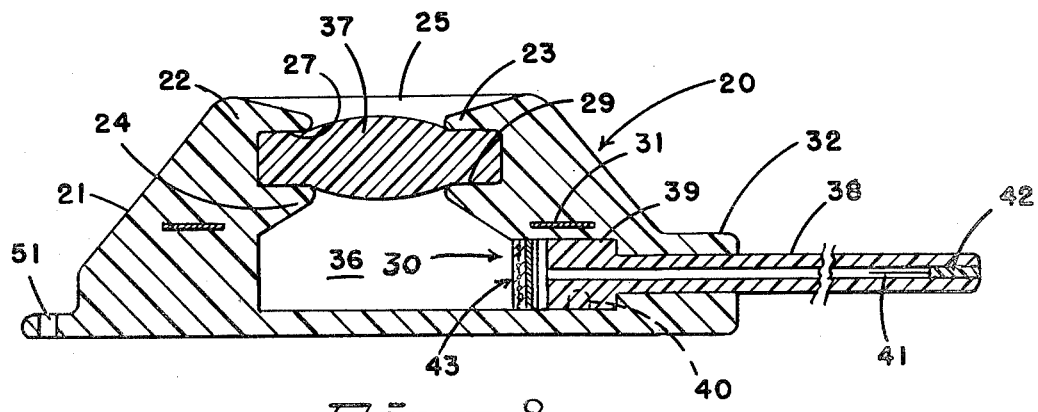

METHOD AND APPARATUS FOR ADMINISTRATION OF FLUIDS

This invention is in the field of medicators; that is, dosing devices for dispensing fluids, such as drugs, to selected sites within a living body. More particularly, this invention relates to apparatus, which includes a fluid receptacle for implantation and means to anchor a transcutaneous fluid conduit, as well as the method of using such apparatus for the long-term administration of therapeutic fluids.

It is known in the art of drug administration to implant a fluid receptacle, including a hollow capsule or container, beneath the skin to be filled from time to time by hypodermic injection with a multidose quantity of a drug and to deliver the drug slowly and continuously, for example, via an outlet catheter or drugpermeable membrane, to a site in the body requiring medication. With this technique, the drug is delivered to the site relatively undiluted by body fluids, and the drug is more effective than when injected intramuscularly or into the blood stream. This is especially the case with certain drugs used in cancer chemotherapy. The technique also has the advantage of decreasing the number of times the skin must be punctured, thereby reducing the risk of trauma and infection.

The same or similar apparatus is also useful in providing samples of fluid from selected sites in the body. In this mode of use, the fluid is collected in the subcutaneous reservoir and withdrawn periodically from the reservoir by hypodermic syringe.

Examples of implantable fluid receptacles include the reservoir disclosed in U.S. Pat. No. 3,310,051, which has a collapsible wall to permit mechanical pumping, and U.S. Pat. No. 3,971,376, which discloses a non-collapsible implantable capsule. The walls of both the aforesaid reservoirs are puncturable by needle, but by reseal upon needle withdrawal. It is also known to include a puncturable, self-sealing rubber septum in the reservoir wall nearest the skin; for example, see U.S. Pat. No. 4,190,048.

Implantable fluid receptacles similar to those just described have been employed in arteriovenous (A-V) shunts for hemodialysis in the management of kidney disease and in cerebrovenous shunts for the treatment of hydrocephalus, for example, as well as in drug therapy. U.S. Pat. No. 3,640,269 and U.S. Pat. No. 3,765,414 disclose the use of receptacles with fluid-permeable membranes, rather than catheters, to deliver the drugs to the body.

The subcutaneous fluid receptacles of the prior art are fed or emptied through the skin. For this purpose a transcutaneous conduit, such as a hollow needle, is inserted through the skin and into the reservoir. A syringe attached to a coupling member on the needle end above the skin is employed to add or remove fluid. The needle is then immediately withdrawn, to be reinserted the next time fluid must be transferred. In those instances in which the therapy is of short duration and the skin need not be punctured too many times this technique can be quite useful.

However, in the event transcutaneous transfers of fluid must be made very often, or where the transcutaneous conduit must remain in place for a long time, the apparatus of the prior art leads to a number of complications. Each needle insertion carries with it the possibility of infection, causes patient trauma, and is likely to core the inlet means, permitting the receptacle to leak, with undesirable results. If the apparatus is used for chemotherapy, for example, many of the chemicals are powerful cytotoxins. Contact of the drugs with tissues remote from the site of treatment cannot be tolerated. Furthermore, after a number of injections it may become impossible to penetrate the skin over the fluid receptacle; fibrosis develops around the multiple needle tracks.

In a number of applications for subcutaneous fluid receptacles it is desirable, in some instances necessary, to maintain transcutaneous connection to the implanted receptacle for a long period of time, hours or days. In these cases, a hypodermic needle inserted through the inlet means and into the reservoir can be secured on the patient's body with adhesive tape or by similar means. But unless the patient is completely immobile, there is danger that the needle may become dislodged, with the prospect of gross damage to the surrounding tissue. An alternative is to lead a rubber catheter from the fluid receptacle through the skin, but there is a great risk of infection with this approach, as well as substantial inconvenience and patient discomfort.

In view of the several deficiences in the apparatus and manner in which implantable fluid receptacles are used, it is evident that an integrated transcutaneous fluid delivery system, which provides not only an improved implantable fluid receptacle, but also a safe, reliable means to anchor a transcutaneous fluid conduit is needed.

The apparatus and the method of its use which constitute this invention overcome many of the problems associated with the previously known transcutaneous fluid delivery systems. The invention provides a convenient mechanism for the long-term delivery of liquid medications with apparatus which is rugged and long-lasting. The invention advantageously minimizes unwanted tissue damage from inadvertent contact with cytotoxic drugs. Use of the invention avoids the infection and other problems associated with repeated needle punctures or prolonged drug feeding through an open wound. Furthermore, the feeding can be interrupted at any time and later restored, if desired, without repenetrating the skin, thereby removing any requirement that the patient remain connected to an external fluid source.

The apparatus of this invention constitutes a fluid receptacle which includes an implantable fluid reservoir, fluid inlet, and fluid outlet means, as well as means to anchor a transcutaneous fluid delivery conduit on the surface of the body. Either the fluid receptacle or the anchor means can be employed separately, but optimum results are obtained by using them in combination as an integrated system.

As an integrated system, this invention comprises a fluid receptacle for subcutaneous implantation in a living body. The receptacle includes a walled reservoir, penetrable, resealable inlet means for adding fluid to the reservoir, and outlet means for delivering fluid from the reservoir to selected sites in the body. The system further comprises an elongated fluid delivery conduit adapted at one end, as with a coupling member, for supercutaneous connection to a supply of the fluid, the other end thereof being adapted for subcutaneous penetration of said inlet means, as well as anchor means for securing the conduit on the body.

Anchor means for a transcutaneous fluid delivery conduit, especially useful in conjunction with the fluid receptacle of this invention, but also with implantable reservoirs of the prior art, for example, the prior art set forth above, comprises a resilient protective boot including a plurality of concentric annular rings having inside and outside peripheries and stacked using the conduit as an axis, beginning with a base ring carrying adhesive for attachment to the body and ending with a terminal ring to be attached to the conduit, optionally via a coupling, each annular ring in the stack being flexibly connected to the next adjacent ring alternately at the inside and outside peripheries to provide shock-absorbing extension and compression along the conduit axis when the terminal ring is attached to the conduit or coupling, as the case may be.

The instant invention also affords a method for the long-term delivery of a therapeutic fluid to sites within a living body, the method comprising implanting in the body a fluid receptacle including a walled reservoir, penetrable, resealable inlet means for adding fluid to the reservoir, and outlet means for delivering fluid from the reservoir to selected sites in the body; penetrating the inlet means with one end of an elongated, hollow fluid delivery conduit adapted at the other end for supercutaneous connection to a supply of the fluid; securing the delivery conduit to the body using the aforesaid anchor means; and connecting the conduit to a supply of the fluid.

The invention, the details of the apparatus, and the manner of its use in practicing the invention will be clarified by referring to the drawings, which illustrate a preferred embodiment having optional features, and the detailed description which follows.

In the drawings:

FIG. 5 and FIG. 6 are side elevation views, in diagrammatic section like FIGS. 3 and 4, showing two other embodiments of the conduit anchor of this invention.

FIG. 7 is a top plan view of a fluid receptacle according to this invention.

FIG. 8 is a side elevation view, in cross-section along line VIII—VIII of FIG. 7.

Figure 1:
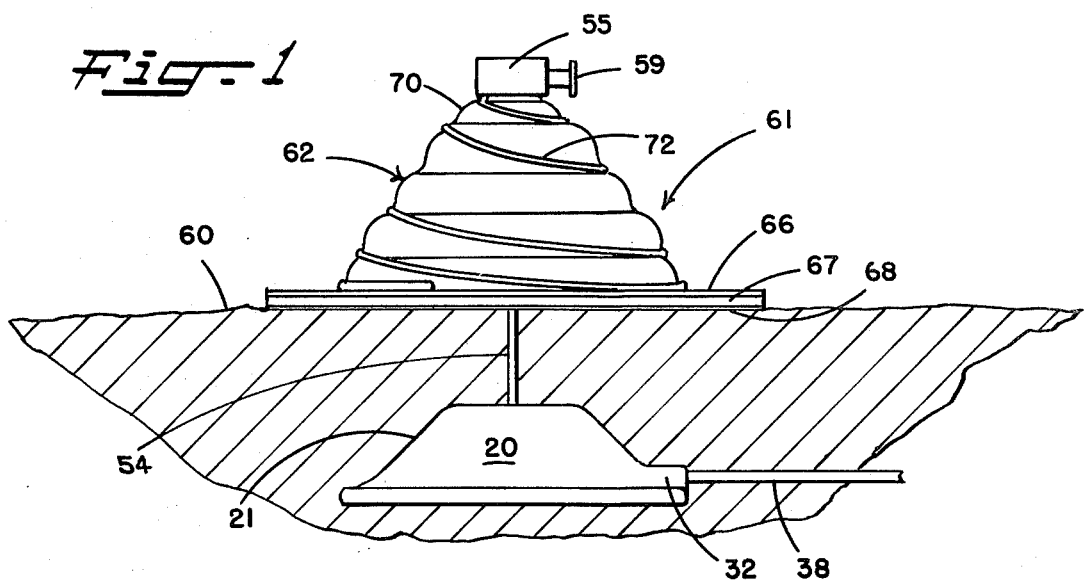
FIG. 1 is a side elevation view showing one embodiment of the integrated transcutaneous fluid delivery system of this invention.

FIG. 1 illustrates one embodiment of the integrated transcutaneous fluid delivery system of this invention in its intended use environment, with fluid receptacle 20 surgically implanted beneath the skin 60 of a living body. The fluid receptacle is placed close enough to the skin to permit one to locate the receptacle by feel. Walled reservoir 21 is volcano-shaped and provides a readily located point of reference. It will be appreciated that the specific size and shape of fluid receptacle 20 are not critical, but it may be of the order 2–3 cm in diameter and 0.5–2 cm high.

Whatever the configuration of fluid receptacle 20, the walls of reservoir 21 are preferably rigid and impermeable to the fluid, except that the fluid inlet means and fluid outlet means, such as catheter 38 in housing 32, are provided. Other, including multiple, inlet and outlet means, such as those described in the prior art, may alternately be employed. Indeed, any of those implantable fluid receptacles of the prior art which include a walled reservoir, penetrable, resealable inlet means for adding fluid to the reservoir, and outlet means for delivering fluid from the reservoir can be employed in the integrated fluid delivery system of this invention.

Still with reference to FIG. 1, fluid receptacle 20 is adapted for subcutaneous penetration by elongated, hollow fluid delivery conduit 54, a hollow needle being one example of such a conduit. Another example of an acceptable conduit is a rubber catheter, which can be inserted, for example, within a hollow needle and the needle then withdrawn. In any case, the fluid delivery conduit is also adapted to pass through skin 60 for supercutaneous connection to a supply of the fluid, as will become apparent.

For long-term use, it is desirable to anchor fluid delivery conduit 54 on the surface of the body. Although adhesive tape and other means known in the prior art can be used, it is preferred to employ the conduit anchor disclosed herein. Referring to FIG. 1, anchor 61, which is above the surface of skin 60, secures conduit 54. Conduit 54 may be mated to coupling 55 as described hereinafter, and thence to a supply of the fluid.

Conduit anchor 61 includes resilient cone-shaped protective boot 62, shown in a somewhat extended position in FIG. 1, with conduit 54 as its axis. The protective boot includes a plurality of connected concentric annular rings, beginning with base ring 66 adapted for attachment to the skin and ending with terminal ring 70, which may be attached to coupling 55. The protective boot is resilient so as to extend and compress along conduit axis 54, but is tensioned, for example, using helical spring 72, to remain compressed, thereby urging compression of protective boot 62 and fluid delivery conduit 54 into reservoir 21, while providing a shock-absorbing construction and a sealed environment about the wound in the skin.

The conduit anchor of this invention is illustrated in greater detail in FIGS. 2 to 6, FIGS. 2–4 being directed to one embodiment, FIGS. 5 and 6 to alternate embodiments.

Figure 2:
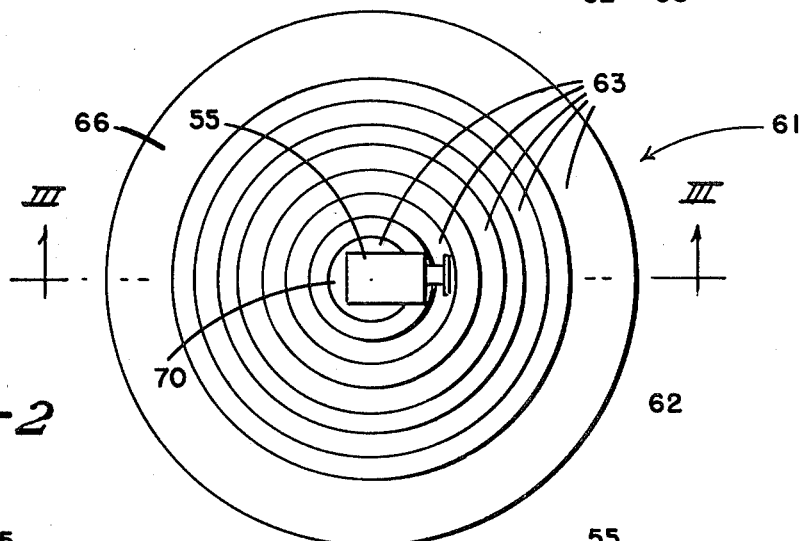
FIG. 2 is a top plan view of a conduit anchor according to this invention.

Referring now to FIG. 2, protective boot 62 includes a plurality of concentric annular rings 63, beginning with base ring 66 and ending with terminal ring 70, which is attached to coupling 55. The protective boot is a resilient construction, conveniently injection molded from a plastic material, for example, a polyolefin as polypropylene about 0.025 cm thick, but base ring 66 may be thicker, to about 0.05 cm, to impart lateral stiffness. When it is produced by molding, the protective boot should be molded with terminal ring 70 compressed toward base ring 66, thereby providing a restoring set urging compression of the protective boot to minimize its vertical profile. Terminal ring 70 is attached to coupling 55 by any of a number of techniques, including solvent or adhesive bonding and ultrasonic welding, but coupling 55 may also be formed as part of the protective boot. Terminal ring 70 may also be attached directly to conduit 54 in the same manner.

Figures 3, 4:
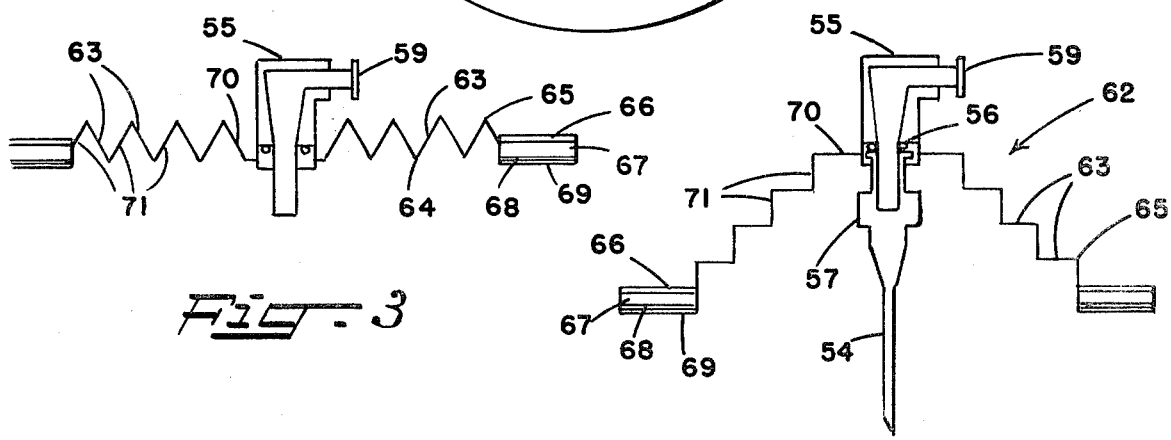
FIG. 3 is a side elevation view, in diagrammatic section along line III—III of FIG. 2.
FIG. 4 is a view like FIG. 3, but showing the protective boot in an extended position and including a fluid delivery conduit.

With reference now to FIG. 3, protective boot 62 is shown in a compressed state. Each annular ring 63 has an inside periphery 64 and an outside periphery 65. In this embodiment the rings are of progressively smaller outside periphery diameter from base ring 66 to terminal ring 70. Each annular ring is flexibly joined by inter-ring connection 71 to the next adjacent ring alternately at inside and outside peripheries.

Base ring 66 carries a medically acceptable adhesive, such as a pressure-sensitive adhesive, for attachment to the patient's skin. For maximum comfort it may be desirable to interpose cushion layer 67, which may be a foam, such as polyurethane foam, between base ring 66 and adhesive layer 68. The exposed adhesive may be protected with removable coating or liner 69 until the conduit anchor is readied for use.

In general, it is preferred to maintain the vertical profile of the conduit anchor as low as possible, for example by urging the protective boot into a compressed state. This may be accomplished, for example, in molding the protective boot and/or by employing spring means 72 attached, for example, to base ring 66 and coupling 55 as described above. The anchor profile can also be decreased by molding conduit 54 with coupling 55 in one piece, thereby avoiding the need for coupling member 57, on one end of conduit 54, and part of coupling 55. Alternately, or additionally, the need for coupling 55 can be avoided altogether by extending conduit 54 to a releasable fitting mounted elsewhere, for example, on base ring 66. Thus, it will be evident that apparatus equivalent to that which includes coupling member 57 and coupling 55, as illustrated herein, is achieved by omitting these elements, thereby providing apparatus in which, for example, terminal ring 70 is attached directly to conduit 54.

FIG. 4 illustrates the conduit anchor of FIGS. 2 and 3, but with protective boot 62 in an extended state, showing annular rings 63 stacked using conduit 54 as the axis. FIG. 4 also shows the conical shape of the protective boot when the annular rings are of progressively smaller outside periphery diameters from the base ring to the terminal ring. Connection of fluid conduit 54, by means of coupling member 57, to coupling 55, and thence by connection 59 to a supply of the fluid, is also shown in FIG. 4. As illustrated, coupling 55 is a 90° male/female Luer lock-type fitting, but any releasable, fluid tight fitting will suffice, for example, of the screw or bayonet type. If Luer lock couplings, well known in the art, are used, O ring 56 may be employed to decrease the probability of a fluid leak. The other end 58 of conduit 54 is preferably equipped with a pencil or Huber tip, if a hollow needle is used, to minimize coring the fluid receptacle inlet means.

In the embodment shown in FIGS. 2-4, each annular ring 63 is substantially flat between its inside and outside peripheries. FIG. 5 illustrates an alternate embodiment wherein each annular ring, other than the base ring, is S-shaped between its inside and outside peripheries. In FIG. 5 protective boot 62 is shown in a compressed state; this type protective boot is shown in an extended state in FIG. 1. Spring means 72, illustrated in FIGS. 1 and 5 only, is an optional feature which can be employed with any of the conduit anchors of this invention. Another embodiment of the conduit anchor of this invention appears in FIG. 6, wherein the annular rings, other than the base ring, have the same outside periphery diameter. In the embodiment of FIG. 6 protective boot 62 describes a cylinder when extended. It will be evident that a number of variations in protective boot 62 are possible.

Referring now to FIGS. 7 and 8, which illustrate a fluid receptacle according to this invention, walled reservoir 21 surrounding cavity 36 is rigid except for penetrable inlet septum 37 and outlet catheter 38. The walled reservoir is conveniently produced from medically acceptable plastics of metals, for example, polysulfone plastic or stainless steel. If the walled reservoir is constructed from plastic, for example, by molding the parts and joining them by ultrasonic welding, it is desirable to incorporate a radiopague locator 31. Suture holes 51, or equivalents, are provided for securing the fluid receptacle beneath the skin.

In order that inlet septum 37 be readily penetrated to introduce fluid into cavity 36, yet reseal itself when fluid conduit 54 is withdrawn, the septum may be constructed of a medically acceptable rubber, such as a silicone rubber. An example of a medically acceptable silicone rubber is Silastic ® Brand silicone rubber, available from Dow Corning Corporation, Midland, Mich. The inlet septum may be a solid rubber block. In that event, it is desirable that it be relatively soft, have a durometer hardness, Shore A scale, or about 45–50, and that the edges of the block be under compression. That is, outer jaw 23 should be spaced from inner jaw 24 a distance sufficient to compress the septum about one-third its unstressed thickness. For example, a circular septum 1.25 cm in diameter and about 0.375 cm thick is compressed to about 0.25 cm thick around its edges.

The septum need not, however, be a unitary elastomeric structure. A laminated sandwich construction is also quite useful. For example, a central, relatively hard, silicone rubber of about 70–80 durometer is joined on either side to a softer layer, about 45–50 durometer, reinforced with an embedded woven polyester or other fabric or titanium screen, and faced on either side with silicone rubber of 45–50 durometer hardness. The layers can be joined with a silicone adhesive. Alternately, any medically acceptable, implantable, penetrable, self-sealing elastomeric material may be used for the septum. Regardless of the details of the septum, fluid reservoir 21 is desirably contoured and provided with tactile crater 25 to facilitate locating the septum beneath the skin.

The outlet means for the fluid, leading from exit port 30 into catheter 38, contains optional features. The catheter 38 is preferably anchored in place at its proximal end in reservoir 21 by means of retainer 39 having ears 40 to engage mating voids in the reservoir. The distal end of the catheter may be open to permit unimpeded flow of the fluid. However, if the distal end of catheter 38 is open, a certain amount of back diffusion of body fluids will occur. The back diffusion can be minimized by locating plug 42 in the catheter distal end and providing slits 41 through the catheter wall, thereby providing a distal check valve. All parts of catheter 38, retainer 39, ears 40, and plug 42 are advantageously produced from medically acceptable silicone rubber molded in one piece.

Figure 10:
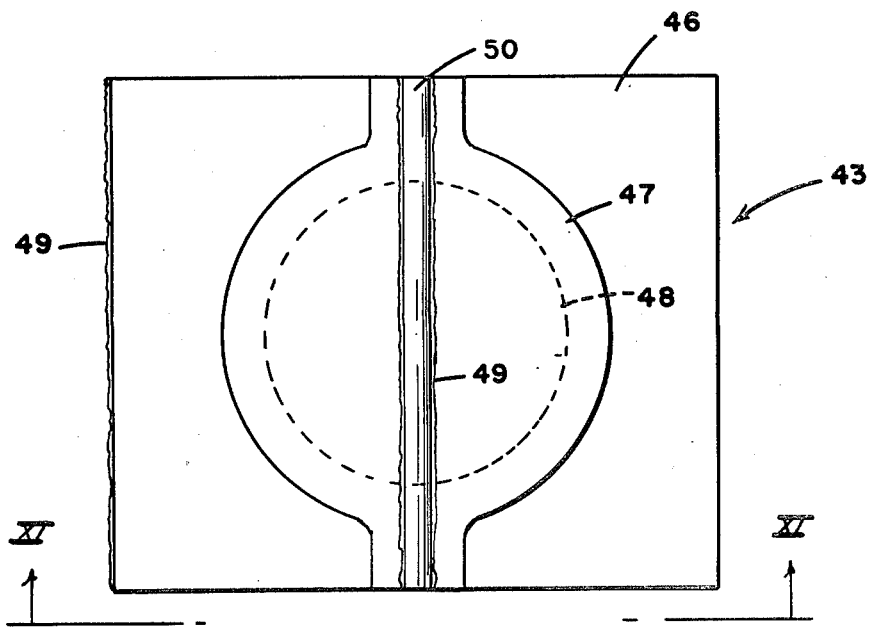
FIG. 10 is a greatly enlarged view of the proximal filter/check valve assembly included in the fluid receptacle shown in FIGS. 7 and 8.
Figure 11:
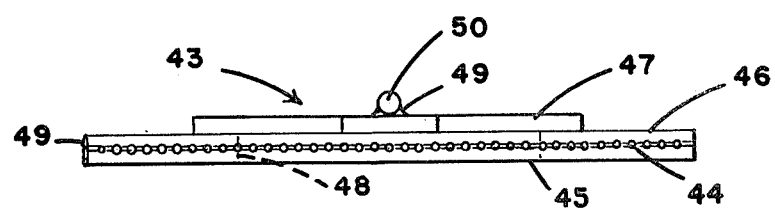
FIG. 11 is an elevation view taken along line XI—XI of FIG. 10.

Proximal filter/check valve assembly 43 is also optionally provided to both minimize back diffusion of body fluids into cavity 36 and prevent solid matter, such as pieces or rubber, tissue, and so forth, from entering catheter 38. The proximal filter/check valve assembly is illustrated in greater detail in FIGS. 10 and 11. Titanium wire mesh screen 44, sandwiched between screen support 45 and valve seat 46, functions as a filter, screen support 45 being positioned immediately adjacent cavity 36. Both the screen support and valve seat, which have passage 48 through them, may be constructed from medically acceptable silicone rubber about 0.025 cm thick. On the downstream side, adjacent valve seat 46, flexible valve flap 47, which may be of the same silicone rubber, is provided. Next downstream is hinge 50, which may be titanium wire, about which valve flap 47 pivots, allowing fluid to pass from cavity 36 into catheter 38. The components of the proximal filter/check valve assembly can be joined together in several ways, for example, by sealing the edges and other points of attachment, such as 49, with a medically acceptable adhesive. A medically acceptable adhesive is, for example, Medical Adhesive A available from Dow Corning Corporation, Midland, Mich.

It will be evident that the presence and location of check valves and filter will depend upon the specific use intended for the fluid receptacle. For example, it may be desirable to locate a filter in the conduit anchor, rather than near exit port 30 to facilitate filter replacement. Further, it may be desired to employ the fluid receptacle to withdraw fluids from the body, in which case the check valves can be reversed or eliminated.

Figure 9:
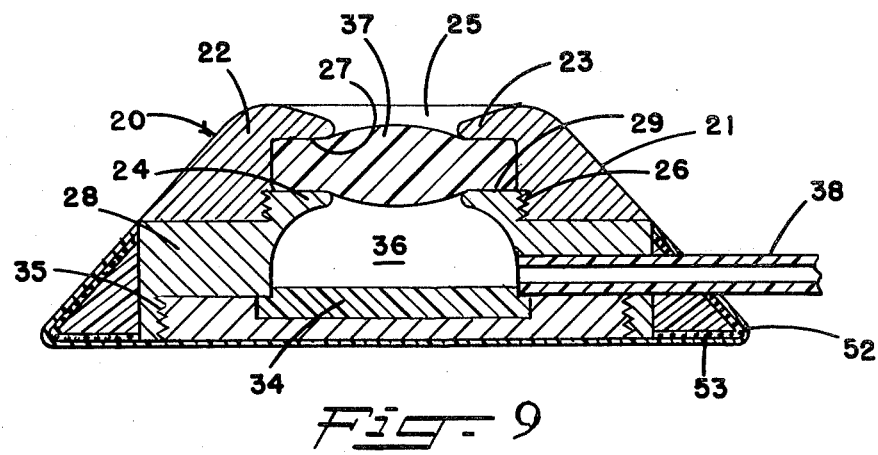
FIG. 9 is a side elevation view, in section like FIG. 8, but illustrating another embodiment of the fluid receptacle of this invention.

FIG. 9 illustrates another embodiment of the fluid receptacle of this invention, an embodiment which is especially suitable for fabrication from a metal, such as stainless steel. In this embodiment it is convenient to produce the walled reservoir in three pieces. The pieces are septum retaining ring 22, reservoir body 28, and base plate 33, threads 35 joining the base plate to the reservoir body and threads 26 joining the septum retaining ring to the reservoir body. In this embodiment, the proper edge compression of septum 37 is attained by adjusting thread 26 to provide the optimum separation between surfaces 27 of the outer jaw and 29 of the inner jaw. Septum 37 performs a secondary role as a gasket between the septum retaining ring and the reservoir body. Another gasket 34, which may be medically acceptable silicone rubber, is provided to seal threads 35 and act as a needle stop, Molded fairing 52 of an elastomeric material such as silicone rubber, with embedded fabric 53 such as polyester, serves as a suture anchor.

It will be apparent that a number of variations in the details of this invention can be made while remaining within the scope of the following claims.

What is claimed is:

1. An integrated transcutaneous fluid delivery system which comprises:

a fluid receptacle for subcutaneous surgical implantation in a living body, said receptacle including a walled reservoir, penetrable resealable inlet means for adding fluid to said reservoir, and outlet means for delivering fluid from said reservoir to selected sites in the body;

an elongated hollow fluid delivery conduit adapted at one end thereof for supercutaneous connection to a supply of the fluid, an other end thereof being adapted for subcutaneous penetration of said inlet means; together with anchor means for securing said conduit on the body including a resilient protective boot including a plurality of concentric annular rings having inside and outside peripheries and stacked using said conduit as an axis beginning with a base ring carrying adhesive for attachment to the body, and ending with a terminal ring to be attached to said conduit, each annular ring in the stack being flexibly joined to the next adjacent ring alternately at said inside and outside peripheries to provide shock-absorbing extension and compression along said axis, and providing means, when said terminal ring and said conduit are attached, to urge said protective boot into a compressed state along said axis, thereby urging said conduit into said reservoir;

whereby implanting said receptacle, penetrating said inlet means with said conduit, and securing said conduit on the body permits long-term infusion of the selected sites with the fluid.

2. The anchor of claim 1 wherein said annular rings are of progressively smaller outside periphery diameters from said base ring to said terminal ring and said protective boot describes a cone when extended along said axis.

3. The anchor of claim 1 wherein said annular rings, other than said base ring, have the same outside periphery diameter and said protective boot describes a cylinder when extended along said axis.

4. The anchor of claim 1 wherein said annular rings are substantially flat between said inlets and outside peripheries.

5. The anchor of claim 1 wherein said rings, other than said base ring, are S-shaped between said inside and outside peripheries.

6. The anchor of claim 1 which further comprises spring means which urge compression of said protective boot along said axis.

7. The anchor of claim 1 wherein said terminal ring and said conduit are joined via a coupling and coupling member.

8. The anchor of claim 7 wherein said coupling is a 90° releasable male/female fitting.

9. An anchor for an elongated hollow transcutaneous fluid delivery conduit which comprises a resilient protective boot including a plurality of concentric annular rings having inside and outside peripheries and stacked using said conduit as an axis, beginning with a base ring carrying adhesive for attachment to the skin of a living body, and ending with a terminal ring to be attached to said conduit, each annular ring in the stack being flexibly connected to the next adjacent ring alternately at inside and outside peripheries to provide shock-absorbing extension and compression along said axis, and providing means, when said terminal ring is attached to said conduit to urge, said protective boot into a compressed state along said axis, thereby urging said conduit into said body.

10. A method for the long-term delivery of a therapeutic fluid to selected sites within a living body which comprises:

implanting in the body a fluid receptacle including a walled reservoir, penetrable resealable inlet means for adding fluid to the reservoir, and outlet means for delivering fluid from the reservoir to the selected sites;

penetrating said inlet means with one end of an elongated hollow fluid delivery conduit adapted at an other end thereof for supercutaneous connection to a supply of the fluid;

securing said conduit on the body with an anchor which includes a resilient protective boot including a plurality of concentric annular rings having inside and outside peripheries and stacked using said conduit as an axis, beginning with a base ring carrying adhesive for attachment to the body, and ending with a terminal ring attached to said conduit, each annular ring in the stack being flexibly joined to the next adjacent ring alternately at inside and outside peripheries to provide shock-absorbing extension and compression along said axis, and providing means to urge said protective boot into a compressed state along said axis, thereby urging said conduit into said reservoir; and connecting said conduit to a supply of the fluid.

11. The anchor of claim 9 wherein said protective boot is molded with said terminal ring compressed toward said base ring, thereby providing a restoring set urging compression of said protective boot to minimize its vertical profile.

* * * * *

UNITED STATES PATENT AND TRADEMARK OFFICE
CERTIFICATE OF CORRECTION

PATENT NO. : 4,464,178
DATED : Aug. 7, 1984
INVENTOR(S) : Michael J. Dalton

It is certified that error appears in the above—identified patent and that said Letters Patent is hereby corrected as shown below:

In column 8, line 12, change "1" to --9--.
In column 8, line 17, change "1" to --9--.
In column 8, line 21, change "1" to --9--.
In column 8, line 22, change "inlets" to --inside--.
In column 8, line 24, change "1" to --9--.
In column 8, line 30, change "1" to --9--.
In column 8, line 33, change "1" to --9--.
In column 8, line 47, change "conduit to" to --conduit, to--.

Signed and Sealed this

Twenty-fifth Day of June 1985

[SEAL]

Attest:

DONALD J. QUIGG

Attesting Officer

Acting Commissioner of Patents and Trademarks